US005413565A

United States Patent [19]

Michels et al.

[11] Patent Number: 5,413,565

[45] Date of Patent: May 9, 1995

[54] GASTROSTOMY FEEDING PORT WITH ELASTIC ADJUSTABLE TIP

[75] Inventors: Lester D. Michels, Eden Prairie; Frederick K. Reuning, Minnetonka, both of Minn.

[73] Assignee: Sandoz Nutrition Ltd., Berne, Switzerland

[21] Appl. No.: 101,883

[22] Filed: Aug. 4, 1993

Related U.S. Application Data

[63] Continuation-in-part of Ser. No. 6,016, Jan. 15, 1993, abandoned.

[51] Int. Cl.[6] .................................. A61M 5/00

[52] U.S. Cl. .................................. 604/247; 604/175; 604/256

[58] Field of Search .................. 604/27, 28, 170, 244, 604/247, 256, 332, 335, 337, 175

[56] References Cited

U.S. PATENT DOCUMENTS

| | | |
|---|---|---|
| D. 328,787 | 8/1992 | Picha et al. . |
| 4,315,513 | 2/1982 | Nawash et al. . |
| 4,344,434 | 8/1982 | Robertson . |
| 4,393,873 | 7/1983 | Nawash et al. . |
| 4,634,421 | 1/1987 | Hegemann . |
| 4,795,430 | 1/1989 | Quinn et al. . |
| 4,834,712 | 5/1989 | Quinn et al. . |
| 4,850,953 | 7/1989 | Haber et al. . |
| 4,863,438 | 9/1989 | Gauderer et al. . |
| 4,944,732 | 7/1990 | Russo . |
| 5,084,014 | 1/1992 | Picha et al. . |
| 5,125,897 | 6/1992 | Quinn et al. . |

*Primary Examiner*—C. Fred Rosenbaum
*Assistant Examiner*—Perry E. Van Over
*Attorney, Agent, or Firm*—Robert S. Honor; Carl W. Battle

[57] ABSTRACT

A gastrostomy feeding port comprising a retaining flange portion, a middle tube portion and elastically adjustable tip portion adaptable to fit a variety of stoma lengths.

14 Claims, 5 Drawing Sheets

GASTROSTOMY FEEDING PORT WITH ELASTIC ADJUSTABLE TIP

This is a continuation-in-part of application Ser. No. 08/006,016 filed Jan. 15, 1993, now abandoned.

BACKGROUND OF THE INVENTION AND INFORMATION DISCLOSURE

This invention relates to gastrostomy feeding ports which are designed to be inserted through an opening in the wall of the abdomen and stomach of a patient for supplying nutrients, medicaments and other fluids to the patient's stomach. These feeding ports are useful in feeding and providing medical treatment to patients who are comatose or otherwise unconscious or unable to orally ingest food or medicine.

U.S. Pat. No. 4,863,438 describes a low profile gastrostomy device which includes a flexible, hollow tube portion having a resiliently deformable mushroom-shaped tip at the inner end and a pair of flat wings at the outer end.

U.S. Pat. No. 4,795,430 describes a device for intubating an ostomy having a fluid delivery lumen, an inflation lumen and an inflatable retention member. The device has a port near one end to dispose the inflation lumen to ambient air and an outlet at the other end to convey fluid from within the fluid delivery lumen into a patient.

U.S. Pat. No 4,834,712 describes a device for angular fixation of a delivery or drainage tube at the point where the tube exits through the skin from a body cavity. The components include a sleeve disposed along the feeding tube and a base elbow unit through which the feeding tube passes. The base elbow unit includes a subdermal portion, a sleeve engaging portion and a cylindrical tube engaging portion.

U.S. Pat. No. 5,084,014 describes a low profile gastrostomy device, for endoscopic placement in an incision provided through the stomach and abdominal walls of a patient, which has a collapsed resilient end portion within a shroud. The device is placed through the incision and the end portion expands to its normal size upon removal of the shroud.

U.S. Pat. No. 328,787 shows the ornamental design for a percutaneous replacement gastrostomy tube.

U.S. Pat. No. 4,944,732 describes a gastrostomy feeding port which includes a deformable conical tip portion having at least one side aperture therethrough, a tube portion extending rearwardly from the tip portion, a fitting portion on the rear end of the tube portion, a removable valve portion in the fitting portion, and a flange portion extending outwardly from the fitting portion.

The present invention is an improvement on the prior art devices, particularly the device of U.S. Pat. No. 4,944,732. The present invention overcomes the deficiency of the prior art devices which were limited to a specific length for each device. Thus, the prior devices were prone to leakage of contents from the stomach through the stoma and inadvertent removal of the device from the stomach. Unlike the prior devices, the present invention is elastically deformable to adjust to a wide variety of stoma lengths.

Thus, it is an object of the present invention to provide a gastrostomy feeding port which is elastically adjustable to a variety of stoma lengths. It is a further object of the present invention to provide a gastrostomy feeding port having the improvement over the feeding port of U.S. Pat. No. 4,944,732 of an elastically adjustable conical tip. It is an even further object of this invention to provide a gastrostomy feeding port comprising in open communication a retaining flange, a middle tube and a tip opposite said flange, wherein said tip has anchoring means connecting said tip to said tube which are elastically deformable toward said tip and engageable with the inner wall of the stomach at various lengths along said tube for preventing the inadvertent removal a pre-established stoma in the stomach.

SUMMARY OF THE INVENTION

This invention relates to a gastrostomy feeding port comprising a retaining flange portion, a middle tube portion and a tip portion; said flange portion being attached to one end of and in open communication with the interior of said tube portion; said tip portion being attached to the end of said tube portion opposite said flange portion, being in open communication with the interior of said tube, being receivable through a pre-established stoma in the stomach of a patient, being operative for passing a fluid into said stomach, and having anchoring means connecting said tip portion to said tube portion; said anchoring means being elastically deformable toward said tip portion and engageable with the inner wall of said stomach at various lengths along said tube portion for preventing the inadvertent removal of said feeding port from said stoma. The feeding port preferably has a valve disposed substantially within said flange portion for permitting the flow of a fluid from said flange portion into said tube portion and for preventing the reverse flow of said fluid. The feeding port is useful in feeding and providing medical treatment to comatose patients or patients who are otherwise unconscious or unable to orally ingest food or medicine.

DETAILED DESCRIPTION

Figure 1:
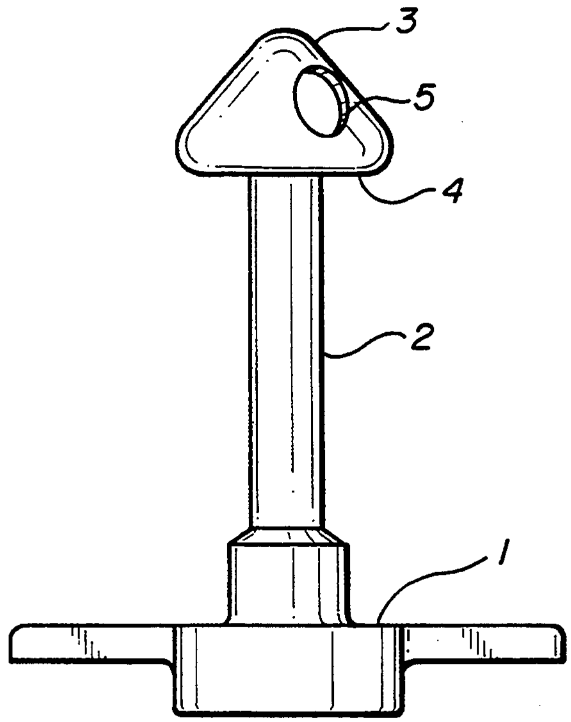
FIG. 1 is an un-scaled side view of an embodiment of the gastrostomy feeding port of this invention.
Figure 2:
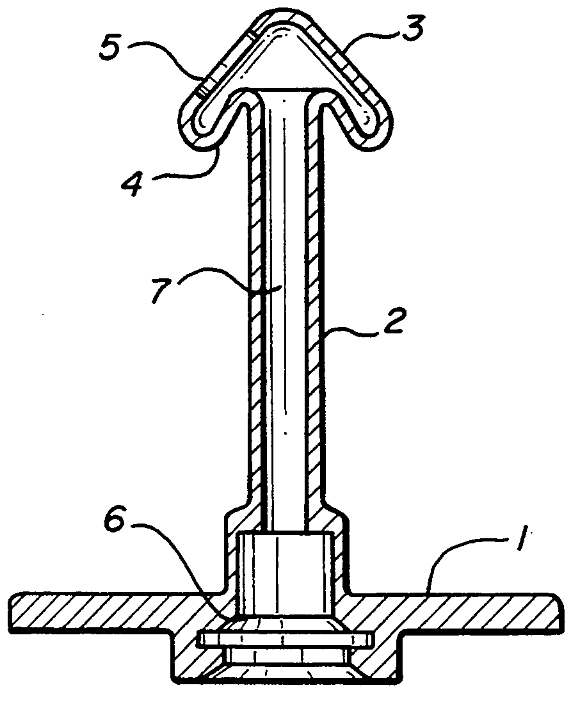
FIG. 2 is an un-scaled, cross-sectional side view of the feeding port.
Figure 3:
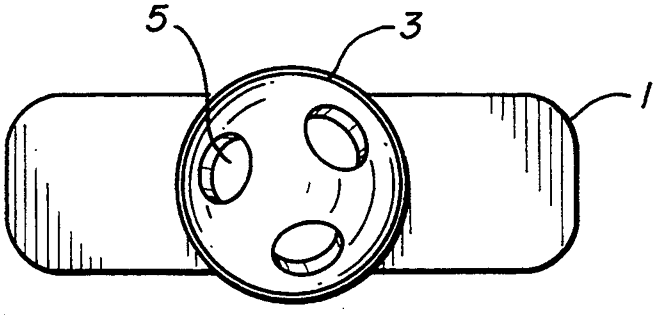
FIG. 3 is an un-scaled top view of the feeding port.
Figure 4:
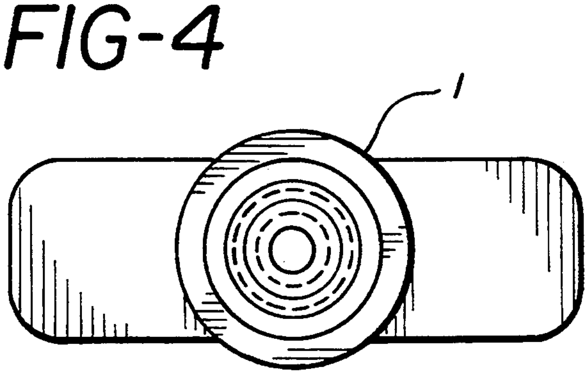
FIG. 4 is an un-scaled bottom view of the feeding port.
Figure 5:
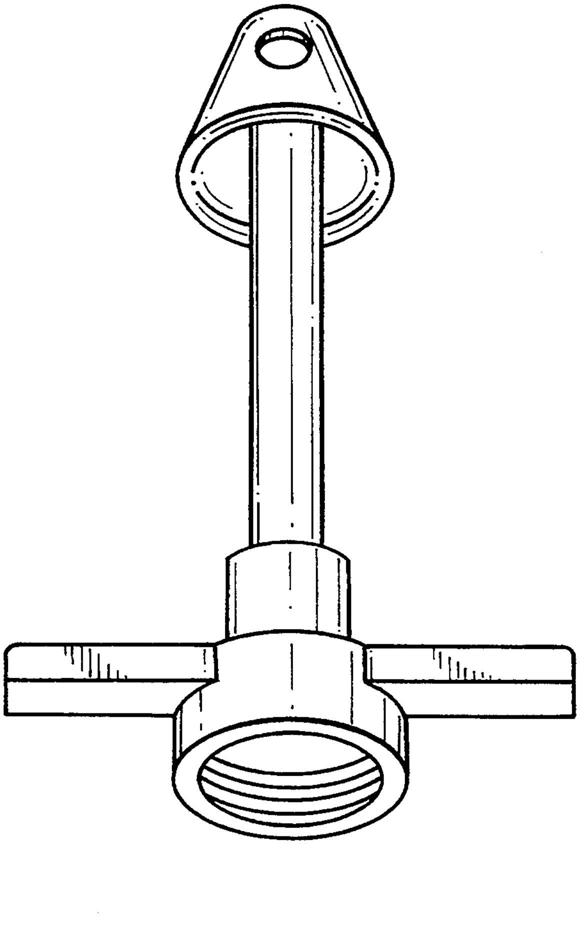
FIG. 5 is an un-scaled perspective view of the feeding port.

A gastrostomy feeding port is provided by the present invention which is resiliently and elastically adjustable to fit a continuous variety of stoma lengths. The feeding port is designed to be inserted through a pre-established stoma in the walls of the abdomen and stomach of a patient for supplying nutrients, medicaments and other fluids to the patient's stomach.

The present invention is an improvement on the feeding port of U.S. Pat. No. 4,944,732, the entire disclosure of which is herein incorporated by reference.

A specific embodiment of the gastrostomy feeding port of this invention as referenced in the drawings comprises a retaining flange portion (1), a middle tube portion (2) and a tip portion (3); said flange portion (1)

being attached to and in open communication with the interior (7) of said tube portion (2); said tip portion (3) being attached to said tube portion (2) opposite said flange portion (1), and being in open communication with the interior (7) of said tube portion (2), and being receivable through a pre-established stoma in the stomach of a patient, and being operative for passing a fluid into said stomach, and said tip portion (3) having anchoring means (4) connecting said tip portion (3) to said tube portion (2); said anchoring means (4) being elastically deformable toward said tip portion (3) and engageable with the inner wall of said stomach at various lengths along said tube portion (2) for preventing the inadvertent removal of said feeding port from said stoma.

The flange portion (1) preferably comprises a pair of leaves extending outwardly from and intergrally formed with a cylindrical housing section. The leaves of the flange portion (1) preferably has a resilent concave configuration which faces toward the tip portion (3). The housing section has an interior cavity therein and a tubular sleeve which extends into the tube portion (2), and is in open communication with the interior (7) of the tube portion. The flange portion (1) is preferably integrally formed from suitable biocompatible plastics or natural or synthetic rubbers, such as, for example, polyurethanes or silicone rubbers. The flange portion (1) preferably has a valve (6) disposed substantially therein, said valve being operative for permitting the flow of a feeding formula or other liquid from the flange portion into the tube portion (2) and for preventing the reverse flow of said liquid. The valve (6) preferably comprises a duck-bill type having converging sides which are resiliently separable to permit the passage of a fluid therethrough in one direction, but not in the reverse direction. The valve preferably is removeably received in the housing section of the flange portion. The flange portion is adapted to receive a male or female connector for connecting the feeding port to a feeding formula supply tube, and preferably has a plug for removeably sealing the feeding port.

The tube portion (2) preferably comprises a hollow tube which is made of resiliently deformable biocompatible plastics or natural or synthetic rubbers. The tube portion is received in and permanently secured to the flange portion (1) and defines an unobstructed passageway into the tip portion (3).

The tip portion (3) can be of any variety of shapes, but preferably is of a hollow conical configuration. The tip portion (3) is in open communication with the interior (7) of said tube portion and is receivable through a pre-established stoma in the stomach of a patient, and is operative for passing a feeding formula or other fluid into the stomach. The tip portion (3) has at its base anchoring means (4) securely connecting the tip portion (3) to the tube portion (2). The anchoring means (4) are elastically deformable toward the tip portion (3) and away from said flange portion (1) so as to be engageable with the inner wall of the stomach at various continuous lengths along the tube portion (2). The anchoring means prevent the inadvertent removal of the feeding port from the stoma in the patient's stomach and allows the feeding port to adjust to a continuous variety of stoma lengths. Preferably the anchoring means (4) are elastically deformable and engageable with the stomach at various lengths from about 0.5 inches to about 2.0 inches along the axis of said tube portion (2) as measured from the flange portion (1). Preferred embodiments have anchoring means which are deformable and engageable with the stomach at stoma lengths of about 0.58–0.88 inches; 0.88–1.18 inches; 1.18–1.48 inches; and 1.48–1.78 inches, respectively. The anchoring means (4) preferably have an overall concave exterior configuration which faces toward the flange portion (1). The tip portion (3) and anchoring means (4) is preferably integrally formed from elastically deformable biocompatible plactics or natural or synthetic rubbers as described earlier.

Figure 6:
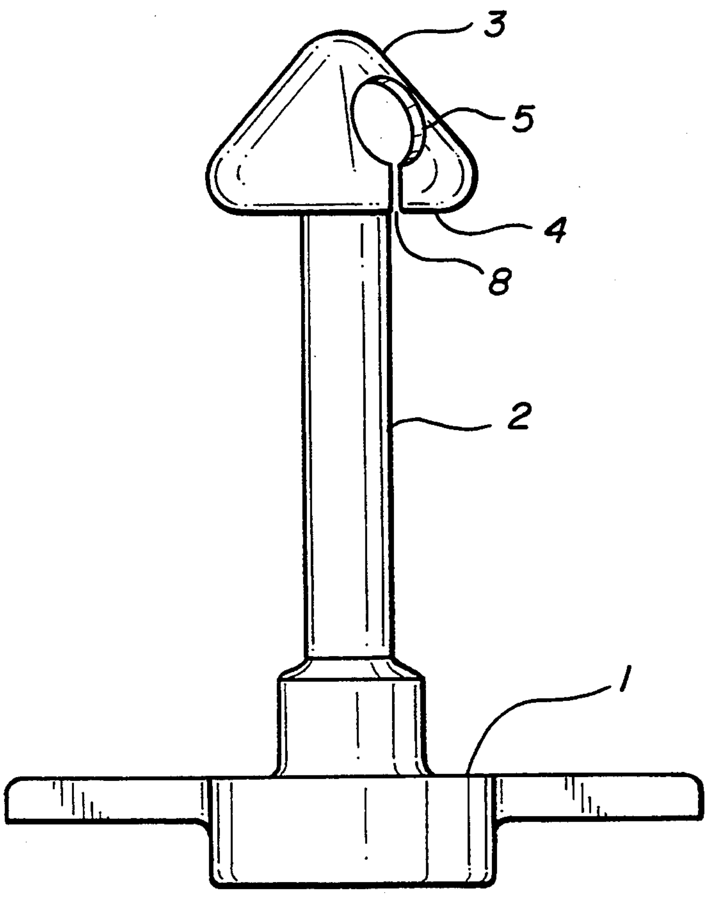
FIG. 6 is an un-scaled side view of the feeding port having slits in the tip portion.
Figure 7:
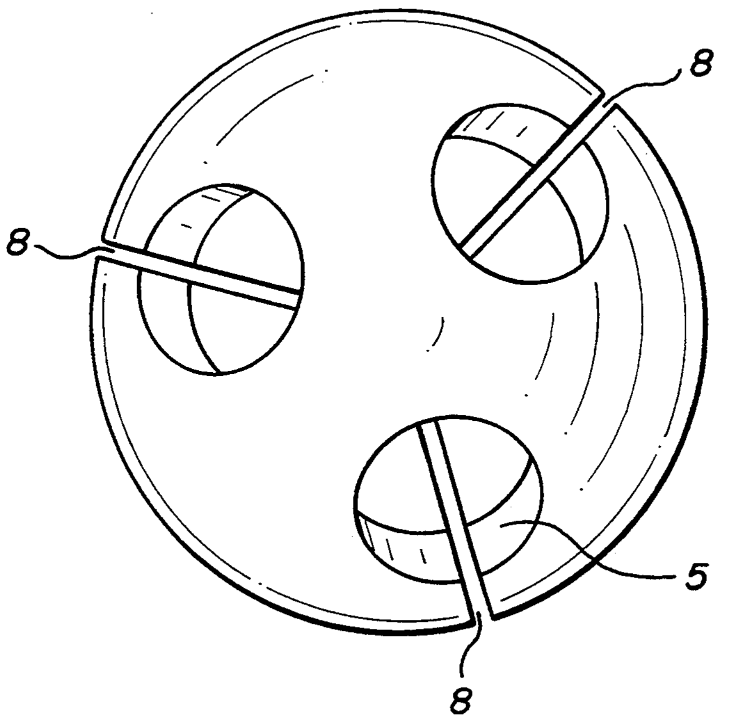
FIG. 7 is an un-scaled top view of the tip portion having a plurality of slits.

In preferred embodiments of the invention, the tip portion preferably has a plurality of slits (8) as shown in FIGS. 6 and 7 which improves the capability of the tip portion and anchoring means to engage the inner wall of the stomach. The tip portion has one or more side apertures (5) through which feeding formula passes from the tip portion into the stomach.

In using the device of the present invention, an obturator comprising an elongated rod having a rounded or blunt end is inserted into the feeding port so that it passes into the tip portion. The tip portion is passed through a pre-established stoma in the abdominal and stomach walls. Once the tip portion has passed into the stomach, the obturator is removed and the tip portion and anchoring means engages the inner wall of the stomach. After the feeding port has been installed in the manner described above, the valve can be installed in the flange portion and a feeding formula supply tube can be connected to the feeding port.

A method useful according to the present invention involves a surgical trocar device to place a gastrostomy port into a patient. The trocar device may be used to create a pathway into the patient's stomach from outside the abdomen, much as a needle trocar is used currently to create a pathway for a pull wire. However, the diameter of the trocar hole is sufficient to allow direct insertion of the gastrostomy port (with a collapsed tip portion), rather than the method of pulling the tube through the esophagus, into the stomach, and out through the puncture wound.

The gastrostomy port with collapsed tip portion are preloaded into a semi-rigid casing tube so that it may be inserted through the trocar tract and into the stomach. Once the end of the casing tube is within the stomach, the tip portion of the gastrostomy port may be pushed out of the casing, allowing the tip portion to expand within the stomach. The casing tube may be removed (as well as any trocar tract tube used), leaving the gastrostomy feeding port in place. The advantages are that placement of the gastrostomy feeding port does not require insertion via the mouth and esophagus.

The embodiments shown and described are illustrative of the invention and various modifications and equivalent embodiments may be made without departing from the scope of this invention.

We claim:

1. A gastrostomy feeding port comprising a retaining flange portion, a middle tube portion and a tip portion; said flange portion being attached to and in open communication with the interior of said tube portion; said tip portion being attached to said tube portion opposite said flange portion, and being in open communication with the interior of said tube portion, and being receivable through a pre-established stoma in the stomach of a patient, and being operative for passing a fluid into said stomach, and said tip portion having at its base anchoring means integrally formed therewith and securely connecting said tip portion to said tube portion;

said anchoring means being elastically deformable toward said tip portion and engageable with the inner wall of said stomach at various lengths along said tube portion for preventing the inadvertent removal of said feeding port from said stoma.

2. A gastrostomy feeding port of claim 1 wherein said tip portion is of hollow conical configuration.

3. A gastrostomy feeding port of claim 1 wherein said flange portion has a valve disposed substantially therein, said valve being operative for permitting the flow of a fluid from said flange portion into said tube portion and for preventing the reverse flow of said fluid.

4. A gastrostomy feeding port of claim 3 wherein said valve comprises a duck-bill type valve.

5. A gastrostomy feeding port of claim 3 wherein said valve is removably received in said flange portion.

6. A gastrostomy feeding port of claim 1 wherein said anchoring means is elastically deformable and engageable with said stomach at various lengths from about 0.5 inches to about 2.0 inches along the axis of said tube portion measured from said flange portion.

7. A gastrostomy feeding port of claim 6 wherein said lengths along the axis of said tube portion is about 0.58–0.88; 0.88–1.18; 1.18–1.48; or 1.48–1.78 inches.

8. A gastrostomy feeding port of claim 1 wherein said tip portion contains one or more side apertures.

9. A gastrostomy feeding port of claim 1 wherein said flange portion has a resilient concave configuration facing toward said tip portion.

10. A gastrostomy feeding port of claim 1 comprised of a plastic or a natural or synthetic rubber.

11. A gastrostomy feeding port of claim 10 comprised of silicone rubber.

12. A gastrostomy feeding port of claim 1 wherein said flange portion contains a plug for removably sealing said feeding port.

13. A gastrostomy feeding port of claim 1 having a plurality of slits in said tip portion.

14. A gastrostomy feeding port of claim 1 in combination with a semi-rigid casing tube wherein said tip portion has been collapsed and said feeding port has been loaded into said semi-rigid casing tube.

* * * * *